(12) United States Patent
Matsushima et al.

(10) Patent No.: US 9,739,703 B2
(45) Date of Patent: Aug. 22, 2017

(54) GRAIN TRANSILLUMINATING DEVICE

(71) Applicant: SATAKE CORPORATION, Tokyo (JP)

(72) Inventors: Hideaki Matsushima, Hiroshima (JP); Hiroki Ishizuki, Hiroshima (JP); Manabu Ikeda, Hiroshima (JP); Jun Zheng, Hiroshima (JP)

(73) Assignee: Satake Corporation, Tokyo (JP)

( * ) Notice: Subject to any disclaimer, the term of this patent is extended or adjusted under 35 U.S.C. 154(b) by 167 days.

(21) Appl. No.: 14/772,775

(22) PCT Filed: Feb. 27, 2014

(86) PCT No.: PCT/JP2014/054786
§ 371 (c)(1),
(2) Date: Sep. 4, 2015

(87) PCT Pub. No.: WO2014/136640
PCT Pub. Date: Sep. 12, 2014

(65) Prior Publication Data
US 2016/0018317 A1 Jan. 21, 2016

(30) Foreign Application Priority Data
Mar. 6, 2013 (JP) .................................. 2013-044355

(51) Int. Cl.
*G01N 21/01* (2006.01)
*G01N 21/85* (2006.01)
*G01N 21/88* (2006.01)

(52) U.S. Cl.
CPC ............. *G01N 21/01* (2013.01); *G01N 21/85* (2013.01); *G01N 21/88* (2013.01); *G01N 2201/022* (2013.01); *G01N 2201/062* (2013.01)

(58) Field of Classification Search
CPC ........ G01N 21/01; G01N 21/85; G01N 21/88; G01N 2201/022; G01N 2201/062
USPC ......................................................... 356/244
See application file for complete search history.

(56) References Cited

U.S. PATENT DOCUMENTS 5,894,345 A 4/1999 Takamoto et al.
6,427,128 B1 7/2002 Satake et al.
(Continued)

FOREIGN PATENT DOCUMENTS

CN 1482457 A 3/2004
CN 101088633 A 12/2007
(Continued)

OTHER PUBLICATIONS

International Prelimiary Report for PCT/JP2014/054786 dated Sep. 8, 2015.
International Search Report for PCT/JP2014/054786 dated Apr. 28, 2014.
Written Opinion for PCT/JP201/054786 dated Apr. 28, 2014.

*Primary Examiner* — Hina F Ayub
(74) *Attorney, Agent, or Firm* — Orion Consulting, Ltd.; Joseph P. Farrar, Esq.

(57) ABSTRACT

An object of the present invention is to provide a grain transilluminating device capable of detecting all of the cracks whose orientations are variously different depending on grains without causing a sample dish to be rotated. According to the present invention, there is provided a grain transilluminating device causing light to enter a transparent bottom face of a sample dish obliquely from a downside, the device including: a base member; a rotary member rotatably disposed in the base member and having a light source on one lateral side, and provided with a reflective plate reflecting the light from the light source toward the bottom face of the sample dish; and a cover member attached onto the base member to constitute, along with the base member, an outer frame and having an opening part positioned above the (Continued)

rotary member to receive the sample dish, wherein an operating part for rotating operation on the rotary member is provided in the rotary member and an opening is formed in the outer frame, and the operating part is configured to extend outside from the outer frame through the opening and to be swingable with a center of the rotary member being an axis.

8 Claims, 5 Drawing Sheets

(56) References Cited

U.S. PATENT DOCUMENTS

| | | | |
|---|---|---|---|
| 2007/0262002 A1 | 11/2007 | Ito et al. | |
| 2008/0184821 A1* | 8/2008 | Greten | G01N 1/20 |
| | | | 73/863 |
| 2009/0147241 A1 | 6/2009 | Shlezinger et al. | |
| 2012/0188786 A1* | 7/2012 | Burges | G01N 21/8806 |
| | | | 362/551 |

FOREIGN PATENT DOCUMENTS

| | | |
|---|---|---|
| CN | 101292152 A | 10/2008 |
| JP | H06-18956 U | 3/1994 |
| JP | H10-160677 A | 6/1998 |
| JP | H10-311797 A | 11/1998 |
| JP | H11-142341 A | 5/1999 |
| JP | 2001-41895 A | 2/2001 |

* cited by examiner

GRAIN TRANSILLUMINATING DEVICE

BACKGROUND

Technical Field

The present invention relates to a grain transilluminating device used for crack inspection or the like of grains such as rice grains.

Background Art

Conventionally, there is known a rice grain transilluminating device which causes light to be transmitted through rice grains for inspecting the presence or absence of a shadow in the rice grain to find cracked rice grains (refer to Patent Document 1).

The rice grain transilluminating device disclosed in Patent Document 1 has a sample dish having a transparent bottom face, a light source causing light to enter the bottom face obliquely, and a housing including the light source and having an upper face provided with an opening receiving the sample dish, wherein the sample dish is rotatably disposed in the opening of the housing.

According to the rice grain transilluminating device, the light can be caused to be transmitted obliquely through a plurality of rice grains placed on the sample dish to detect cracks on the basis of shadows appearing in the rice grains. Moreover, according to the rice grain transilluminating device, since the positions of the rice grains can be changed with respect to the travelling direction of the light by manually rotating the sample dish, all of the cracks whose orientations are variously different depending on the rice grains can be detected.

In the above-mentioned conventional rice grain transilluminating device, the sample dish is rotated to move the rice grains. Therefore, even if a cracked rice grain has been once able to be found, there is a concern that which rice grain is the cracked rice grain is lost in the next stage.

CITATION LIST

Patent Literature

Patent Document 1

Japanese Patent Application Laid-Open No. H10-160677

SUMMARY OF INVENTION

Technical Problem

Therefore, an object of the present invention is to provide a grain transilluminating device capable of detecting all of the cracks whose orientations are variously different depending on grains without causing a sample dish to be rotated.

Solution to Problem

To achieve the above-mentioned object, there is provided according to the present invention a grain transilluminating device causing light to enter a transparent bottom face of a sample dish obliquely from a downside, the device including:

a base member;

a rotary member rotatably disposed in the base member and having a light source on one lateral side; and a cover member attached onto the base member to constitute, along with the base member, an outer frame and having an opening part positioned above the rotary member to receive the sample dish, wherein an operating part for rotating operation on the rotary member is provided in the rotary member and an opening is formed in the outer frame, and the operating part is configured to extend outside from the outer frame through the opening and to be swingable with a center of the rotary member being an axis.

In the grain transilluminating device according to the present invention, the opening is preferably a slit-shaped opening and is formed on a lateral face of the outer frame, and the operating part is configured to be swingable along the slit-shaped opening.

In the grain transilluminating device according to the present invention, the opening is preferably a slit-shaped opening and is formed on an upper face of the cover member, and the operating part is configured to be swingable along the slit-shaped opening.

In the grain transilluminating device according to the present invention, a reflective plate reflecting the light from the light source toward a bottom face of the sample dish received by the opening part of the cover member is preferably provided in the rotary member.

In the grain transilluminating device according to the present invention, a recess part enabling a discharging part of the sample dish to be received is preferably provided sidewise from the opening part on an upper face of the cover member.

In the grain transilluminating device according to the present invention, the recess part is preferably provided in pairs at positions in symmetry with respect to a straight line connecting a center of the opening part and a center of the slit-shaped opening in plan view.

In the grain transilluminating device according to the present invention, the operating part is preferably provided further outward of the one lateral side having the light source in the rotary member.

In the grain transilluminating device according to the present invention, a bottom part formed of a transparent material is preferably provided in the opening part of the cover member.

Advantageous Effect of Invention

In the grain transilluminating device according to the present invention, operation of the operating part extending outside from the outer frame through the opening causes the rotary member having the light source on one lateral side to rotate. Therefore, all of the cracks whose orientations are variously different depending on grains can be detected without causing the sample dish to be rotated.

According to the grain transilluminating device according to the present invention, in inspection of cracks, the positions of the grains do not move as seen by the operator. Therefore, the operator does not lose sight of cracked grains, which have been once found, in the following stage, and the problem of occurrence of errors in counting the cracked grains does not arise.

In the grain transilluminating device according to the present invention, since the operating part provided in the rotary member is caused to extend outside through the opening formed in the outer frame, the structure is extremely simple.

In the grain transilluminating device according to the present invention, the recess part enabling the discharging part of the sample dish to be received can be formed sidewise from the opening part on the upper face of the cover member. By doing so, even in the case where the sample dish that has the discharging part extending sidewise is used, the discharging part does not become an obstacle when the sample dish is placed onto the grain transilluminating device.

In the grain transilluminating device according to the present invention, not the sample dish but the rotary member having the light source on one lateral side is rotated. Therefore, the discharging part of the sample dish does not become an obstacle, and all of the cracks whose orientations are variously different depending on grains can be detected.

In the grain transilluminating device according to the present invention, the pair of recess parts can be provided in symmetry with respect to the straight line connecting the center of the opening part and the center of the slit-shaped opening in plan view. By doing so, the operation can be smoothly performed no matter which of the right and the left is the handedness of the operator.

In the grain transilluminating device according to the present invention, the operating part provided in the rotary member can be further outside of the one lateral side having the light source in the rotary member. By doing so, since the operator can perform rotating operation on the rotary member with feeling as if he/she grabs a light source in hand, cracks can be easily checked.

DETAILED DESCRIPTION OF EMBODIMENTS

Embodiments of the present invention are described based on the drawings.

Figure 1:
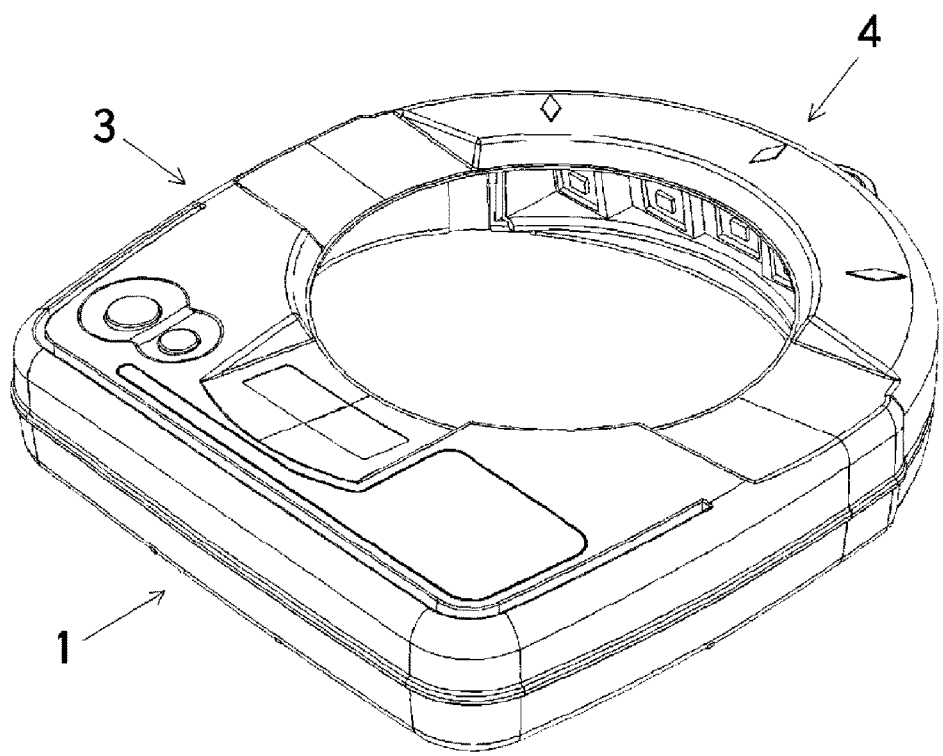
FIG. 1 is a perspective view of a grain transilluminating device in an embodiment of the present invention as seen from the backside.
Figure 2:
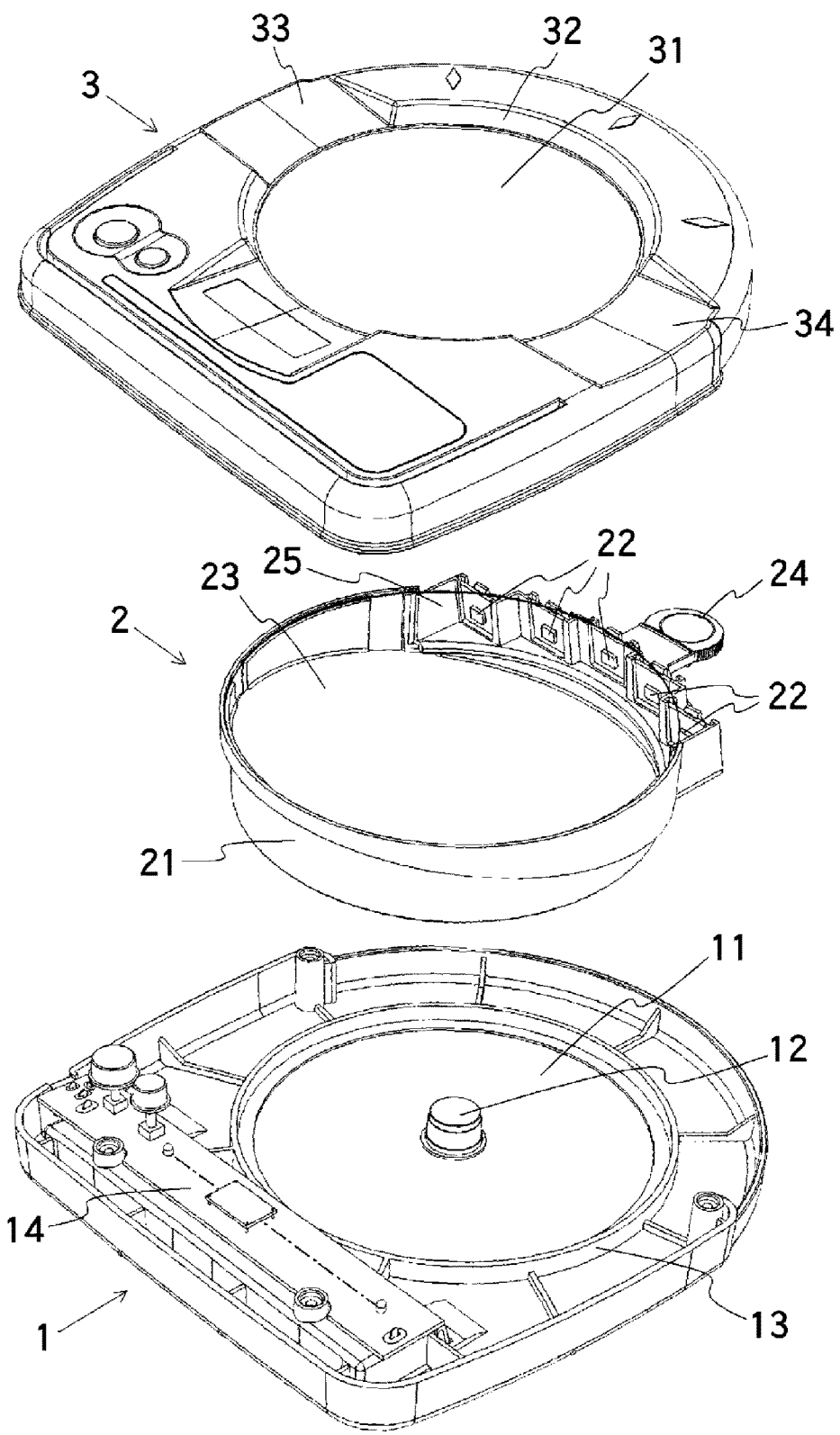
FIG. 2 is an exploded perspective view of the grain transilluminating device in FIG. 1.
Figure 3:
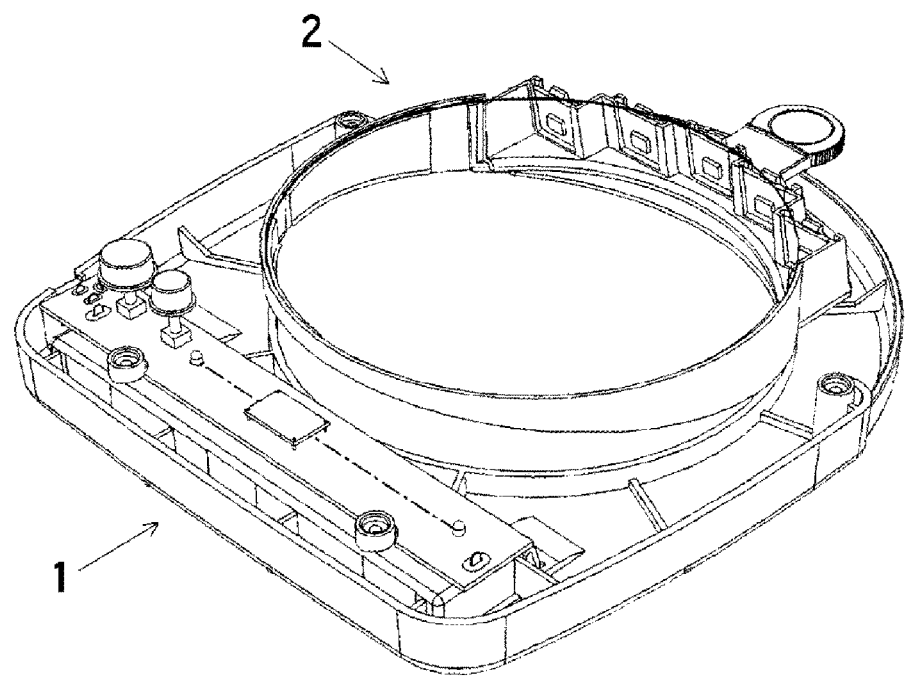
FIG. 3 is an explanatory drawing of a state where a cover is taken off in the grain transilluminating device of FIG. 1.

FIG. 1 illustrates a perspective view of a grain transilluminating device in an embodiment of the present invention as seen from the backside. FIG. 2 illustrates an exploded perspective view of the grain transilluminating device in FIG. 1. FIG. 3 illustrates an explanatory drawing of a state where a cover is taken off in the grain transilluminating device of FIG. 1.

The grain transilluminating device in the present embodiment includes a base 1, a rotary drum 2 and a cover 3.

In the base 1, a supporting part 11 rotatably supporting the rotary drum 2 is formed. The supporting part 11 has a circular projection part 12 to which a recess part formed at the bottom part center of the rotary drum 2 is rotatably loosely fitted, and a circular guide 13 guiding the outer circumferential face of a drum main body 21 mentioned later.

Moreover, in the base 1, a power supply device and the like 14 for lighting light sources disposed in the rotary drum 2 is included.

The rotary drum 2 has a cylindrical drum main body 21, LED light sources 22 disposed outward of one lateral part of the drum main body 21, a reflective plate 23 disposed inside the drum main body 21 and reflecting light from the LED light sources 22 upward, a lever 24 provided on the outside of the LED light sources 22 for rotating operation on the rotary drum 2. A transparent cover 25 intervenes between the drum main body 21 and the LED light sources 22. Moreover, a not-shown recess part is formed at the bottom part center of the rotary drum 2. The not-shown recess part is rotatably loosely fitted to the circular projection part 12 of the base 1. Herein, the transparent cover 25 is for preventing the operator from directly touching the LED light sources 22, and plays a role on prevention of electric shock or heat shock.

Herein, while an example in which the plurality of LED light sources 22 are disposed into an arc shape is presented, a single LED light source 22 may be disposed. Moreover, bluish white LED light sources are preferably used for the LED light sources 22, a black reflective plate made from a resin plate or the like is preferably used for the reflective plate 23. Furthermore, preferably, the LED light sources 22 are disposed such that the optical axis falls within a range of 0 to 10 degrees downward with respect to the horizontal direction, and the reflective plate 23 is disposed to incline in an orientation opposing the LED light sources 22 in such a manner that the angle thereof falls within a range of 10 degrees to 35 degrees with respect to the horizontal direction.

When the bluish white LED light sources are used for the LED light sources 22 and the black reflective plate is used for the reflective plate 23, since in inspection of polished rice, a shadow of a crack is clearly present as a black line in a rice grain, visual check can be made easy.

In the cover 3, an opening part 31 receiving a sample dish is formed. The opening part 31 is positioned upward of the rotary drum 2 in the state where the grain transilluminating device is assembled, the periphery of the opening part 31 has a tapered face 32. Further, when the sample dish is placed onto the grain transilluminating device, the sample dish can be received in the stable state by the opening part 31 including the tapered face 32. Notably, in the opening part 31, a bottom part formed of a transparent material can also be provided.

On the upper face of the cover 3, recess parts 33 and 34 extending sidewise from the opening part 31 are formed and configured to be able to receive a discharge part of the sample dish. While at least one of the recess parts 33 and 34 only has to be formed, a pair of these is preferably formed at positions in symmetry with respect to a straight line connecting the center of the opening part 31 and the center of a slit-shaped opening 41 mentioned later in plan view.

Figure 4:
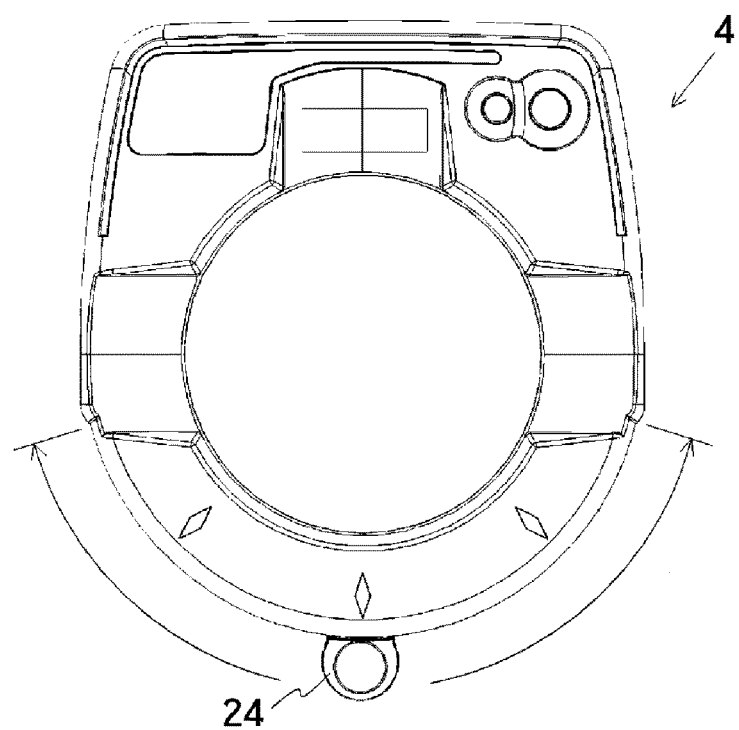
FIG. 4 is a plan view of the grain transilluminating device in FIG. 1.
Figure 5:
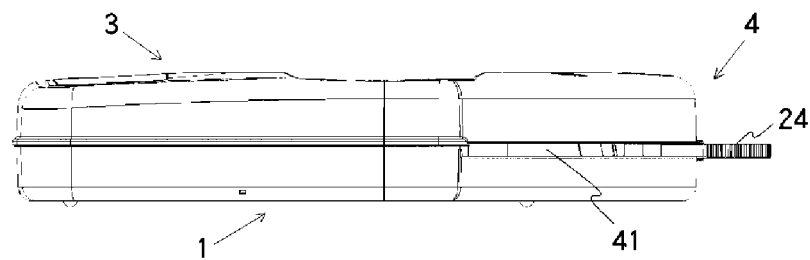
FIG. 5 is a left side view of the grain transilluminating device in FIG. 1.
Figure 6:
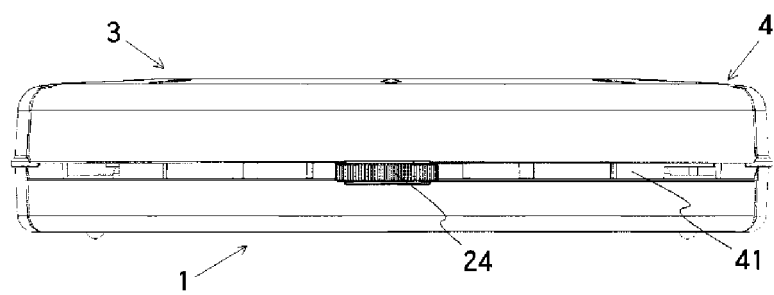
FIG. 6 is an elevation view of the grain transilluminating device in FIG. 1.

FIG. 4 illustrates a plan view of the grain transilluminating device in FIG. 1. FIG. 5 illustrates a left side view of the grain transilluminating device in FIG. 1. FIG. 6 illustrates an elevation view of the grain transilluminating device in FIG. 1.

The grain transilluminating device in the embodiment of the present invention constitutes an outer frame 4 by attaching the cover 3 onto the base 1.

As illustrated in FIG. 4, the lever 24 of the rotary drum 2 extends outside from the outer frame 4. Moreover, the outer frame 4 is configured to be an arc shape at least on the side where the lever 24 extends outside.

As illustrated in FIG. 5 and FIG. 6, in the outer frame 4, the slit-shaped opening 41 is formed. The slit-shaped opening 41 is formed on the lateral face between the base 1 and the cover 3 over a predetermined range. The lever 24 extends outside from the outer frame 4 through the slit-shaped opening 41. The lever 24 is configured to be swingable by a predetermined angle along the slit-shaped opening 41 with the center of the rotary drum 2 being the axis. Herein, the lever 24 is configured to be swingable over a range of at least 90 degrees, preferably 135 degrees or more.

Notably, the lever 24 is here configured to extend outside from the outer frame 4 through the slit-shaped opening 41 formed on the lateral face between the base 1 and the cover 3. Instead, a slit-shaped opening can also be formed into an arc shape on the upper lateral face of the cover 3 to form the lever 24 into an L shape as laterally seen, and thereby, the lever 24 can also be caused to extend outside from the outer frame 4 through the slit-shaped opening formed into the arc shape. Further, also in this case, the lever 24 is configured to be swingable over a range of at least 90 degrees, preferably 135 degrees or more.

Figure 7:
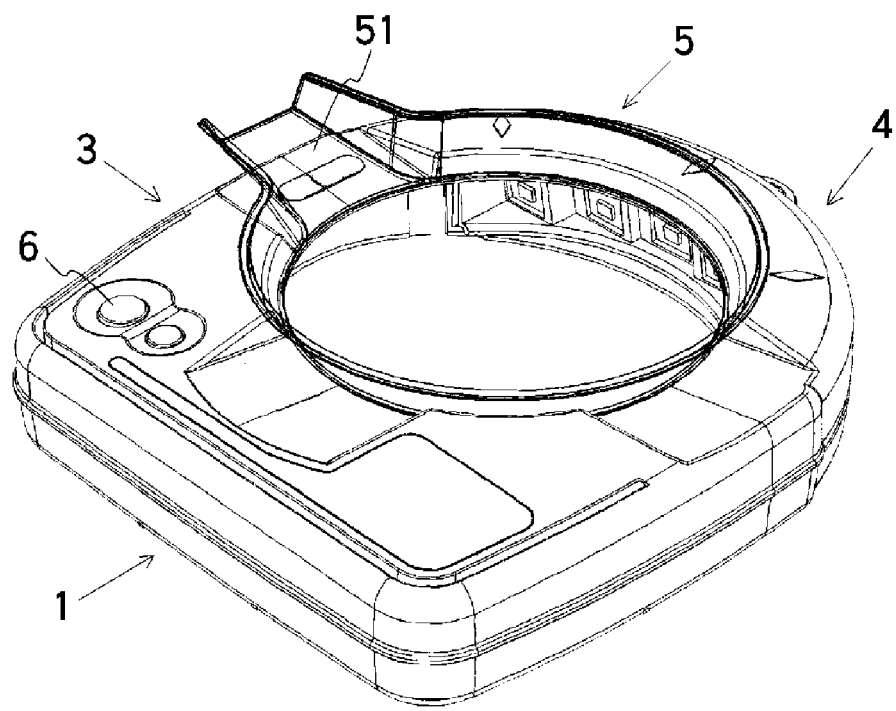
FIG. 7 is a perspective view of a state where a sample dish is placed onto the grain transilluminating device in the embodiment of the present invention as seen from the backside.
Figure 8:
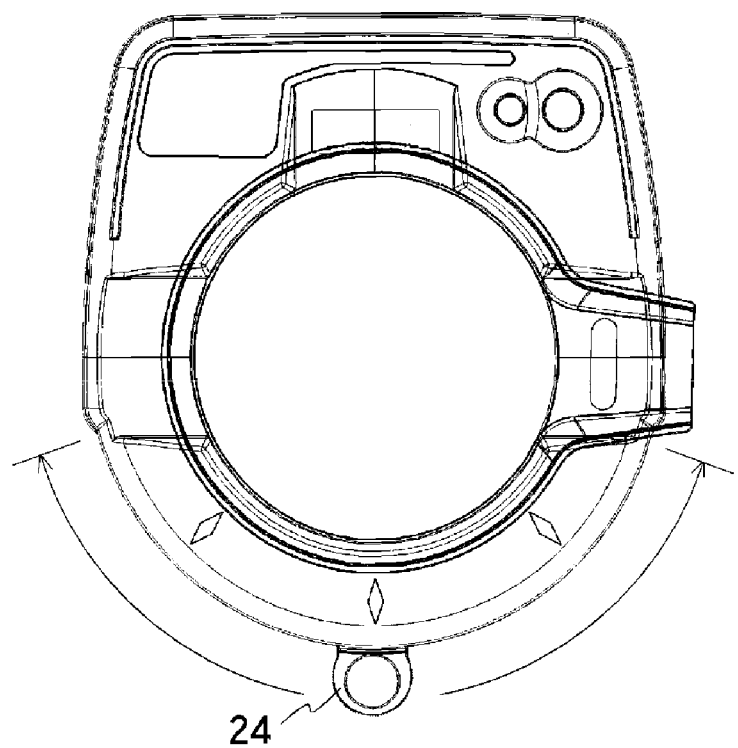
FIG. 8 is a plan view of the state where the sample dish is placed onto the grain transilluminating device in the embodiment of the present invention.

FIG. 7 illustrates a perspective view of the state where the sample dish is placed onto the grain transilluminating device in the embodiment of the present invention as seen from the backside. FIG. 8 illustrates a plan view of the state where the sample dish is placed onto the grain transilluminating device in the embodiment of the present invention.

When crack inspection of rice grains is performed using the grain transilluminating device in the embodiment of the present invention, a plurality of rice grains are first placed on the sample dish 5 in which at least the bottom face thereof is formed of a transparent material. Next, the sample dish 5 is placed onto the opening part 31 formed in the cover 3. In this stage, since the opening part 31 has the tapered face 32 on its periphery, the sample dish 5 can be received in the stable state.

Next, a power supply button 6 of the grain transilluminating device undergoes ON-operation to light the LED light sources 22. Light of the lit LED light sources 22 directly enters the bottom face of the sample dish 5, or is reflected by the reflective plate 23 to enter the bottom face of the sample dish 5 obliquely from the downside and is transmitted through the plurality of rice grains placed on the sample dish 5. In this stage, since when a crack is present in the rice grain, a shadow arises to show a black line, the operator can find cracked rice grains.

Then, swinging operation on the lever 24 of the rotary drum 2 is performed to rotate the rotary drum 2. By doing so, the light of the LED light sources 22 is to enter the plurality of rice grains at a different angle, and all of the cracks whose orientations are variously different depending on the rice grains can be detected.

In the grain transilluminating device in the embodiment of the present invention, since the rotary drum 2 is rotated, the positions of the rice grains do not move as seen by the operator.

Accordingly, according to the grain transilluminating device in the embodiment of the present invention, the operator does not lose sight of the cracked rice grains, which have been once found, in the following stage, and the problem of occurrence of errors in counting the cracked rice grains does not arise.

Moreover, in the grain transilluminating device in the embodiment of the present invention, since the slit-shaped opening 41 is formed on the lateral face between the base 1 and the cover 3 or on the upper face lateral side of the cover 3, and the lever 24 provided in the rotary drum 2 is caused to extend outside from the outer frame 4 through the slit-shaped opening 41, the structure is extremely simple.

In the grain transilluminating device in the embodiment of the present invention, the recess parts 33 and 34 extending sidewise from the opening part 31 are formed on the upper face of the cover 3. Therefore, as illustrated in FIG. 7 and FIG. 8, even in the case where the sample dish 5 has the discharging part 51 extending sidewise, the discharging part 51 does not become an obstacle when the sample dish 5 is placed onto the grain transilluminating device.

When the sample dish 5 is to be rotated as in a conventional rice grain transilluminating device, the discharging part 51 becomes an obstacle. In the grain transilluminating device in the embodiment of the present invention, not the sample dish 5 but the rotary drum 2 having the LED light sources 22 is rotated. Therefore, the discharging part 51 of the sample dish 5 does not become an obstacle, and all of the cracks whose orientations are variously different depending on the rice grains can be detected.

In the grain transilluminating device in the embodiment of the present invention, the pair of recess parts 33 and 34 extending sidewise from the opening part 31 can also be formed on the upper face of the cover 3. By doing so, the operation can be easily performed irrespective of the handedness of the operator. Moreover, the pair of recess parts 33 and 34 can also be formed at positions in symmetry with respect to a straight line connecting the center of the opening part 31 and the center of the slit-shaped opening 41 in plan view. By doing so, the operation can be smoothly performed no matter which of the right and the left is the handedness of the operator.

In the grain transilluminating device in the embodiment of the present invention, the lever 24 provided in the rotary drum 2 is not necessarily provided on the same side as that of the LED light sources 22. When the lever 24 is provided on the same side as that of the LED light sources 22 in the rotary drum 2, since the operator can perform rotating operation on the rotary member with feeling as if he/she grabs a light source in hand, cracks can be easily checked.

The grain transilluminating device in the embodiment of the present invention can be used for all kinds of grains, which are not limited to rice grains, and moreover, can also be used for inspection other than that of cracks.

The present invention is not limited to the above-mentioned embodiment, and it goes without saying that the configuration can be properly modified without departing from the scope of the invention.

INDUSTRIAL APPLICABILITY

The grain transilluminating device of the present invention has excellent practicability since all of the cracks whose orientations are variously different depending on the grains can be detected without causing the sample dish to be rotated.

REFERENCE SIGNS LIST

1 Base
11 Supporting part
12 Circular projection part
13 Circular guide
2 Rotary drum
21 Drum main body
22 LED light source 23 Reflective plate
24 Lever
25 Transparent cover
3 Cover
31 Opening part
32 Tapered face
33 Recess part
34 Recess part
4 Outer frame of the grain transilluminating device
41 Slit-shaped opening
5 Sample dish
51 Discharging part
6 Power supply button

What is claimed is:

1. A grain transilluminating device causing light to enter a transparent bottom face of a sample dish obliquely from a downside, the device comprising:
   a base member;
   a rotary member rotatably disposed in the base member and having a light source on one lateral side; and
   a cover member attached onto the base member to constitute, along with the base member, an outer frame and having an opening part positioned above the rotary member to receive the sample dish, wherein
   an operating part for rotating operation on the rotary member is provided in the rotary member and an opening is formed in the outer frame, and
   the operating part is configured to extend outside from the outer frame through the opening and to be swingable with a center of the rotary member being an axis.

2. The grain transilluminating device according to claim 1, wherein the opening is a slit-shaped opening and is formed on a lateral face of the outer frame, and the operating part is configured to be swingable along the slit-shaped opening.

3. The grain transilluminating device according to claim 1, wherein the opening is a slit-shaped opening and is formed on an upper face of the cover member, and the operating part is configured to be swingable along the slit-shaped opening.

4. The grain transilluminating device according to claim 1, wherein a reflective plate reflecting the light from the light source toward a bottom face of the sample dish received by the opening part of the cover member is provided in the rotary member.

5. The grain transilluminating device according to claim 1, wherein a recess part enabling a discharging part of the sample dish to be received is provided sidewise from the opening part on an upper face of the cover member.

6. The grain transilluminating device according to claim 5, wherein the recess part is provided in pairs at positions in symmetry with respect to a straight line connecting a center of the opening part and a center of the slit-shaped opening in plan view.

7. The grain transilluminating device according to claim 1, wherein the operating part is provided further outward of the one lateral side having the light source in the rotary member.

8. The grain transilluminating device according to claim 1, wherein a bottom part formed of a transparent material is provided in the opening part of the cover member.

* * * * *